(12) United States Patent
Insaidoo et al.

(10) Patent No.: US 11,515,007 B2
(45) Date of Patent: Nov. 29, 2022

(54) IN SILICO PROCESS FOR SELECTING PROTEIN FORMULATION EXCIPIENTS

(71) Applicants: Merck Sharp & Dohme Corp., Rahway, NJ (US); Francis Insaidoo, Rahway, NJ (US); David Roush, Colts Neck, NJ (US)

(72) Inventors: Francis Insaidoo, Rahway, NJ (US); David Roush, Colts Neck, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 1037 days.

(21) Appl. No.: 16/081,102

(22) PCT Filed: Mar. 6, 2017

(86) PCT No.: PCT/US2017/020847
§ 371 (c)(1),
(2) Date: Aug. 30, 2018

(87) PCT Pub. No.: WO2017/155840
PCT Pub. Date: Sep. 14, 2017

(65) Prior Publication Data
US 2019/0062948 A1     Feb. 28, 2019

Related U.S. Application Data

(60) Provisional application No. 62/307,006, filed on Mar. 11, 2016.

(51) Int. Cl.
*G01N 33/48*     (2006.01)
*G01N 33/50*     (2006.01)
(Continued)

(52) U.S. Cl.
CPC ......... *G16B 35/00* (2019.02); *G01N 33/6803* (2013.01); *G16B 5/00* (2019.02);
(Continued)

(58) Field of Classification Search
CPC ........ G16B 35/00; G16B 15/30; G16B 50/20; G16B 5/00; G16B 45/00; G16B 15/00; G16B 35/20; G16C 20/60; G01N 33/6803
See application file for complete search history.

(56) References Cited

U.S. PATENT DOCUMENTS 5,436,850 A    7/1995   Eisenberg et al.
5,878,373 A    3/1999   Cohen et al.
(Continued)

FOREIGN PATENT DOCUMENTS

JP     2016166159 A    9/2016
WO    WO2011050864 A1   5/2011

OTHER PUBLICATIONS

Sheinerman et al. On the role of electrostatic interactions in the design of protein-protein interfaces. Journal of Molecular Biology, vol. 318, pp. 161-177. (Year: 2002).*

(Continued)

*Primary Examiner* — Russell S Negin
(74) *Attorney, Agent, or Firm* — Steven C. Pageau; Anna L. Cocuzzo (57) ABSTRACT

The invention relates to an in silico screening method to identify candidate excipients for reducing aggregation of a protein in a formulation. The method combines computational molecular modeling and molecular dynamics simulations to identify sites on a protein where non-specific self-interaction and interaction of different test excipients may occur, determine the relative binding energies of such interactions, and select one or more test excipients that meet specified interaction criteria for use as candidate excipients in empirical screening studies.

13 Claims, 7 Drawing Sheets

(51) Int. Cl.
   G16B 35/00    (2019.01)
   G01N 33/68    (2006.01)
   G16C 20/60    (2019.01)
   G16B 15/00    (2019.01)
   G16B 50/20    (2019.01)
   G16B 15/30    (2019.01)
   G16B 5/00     (2019.01)
   G16B 45/00    (2019.01)
   G16B 35/20    (2019.01)

(52) U.S. Cl.
   CPC ............. *G16B 15/00* (2019.02); *G16B 15/30* (2019.02); *G16B 45/00* (2019.02); *G16B 50/20* (2019.02); *G16C 20/60* (2019.02); *G16B 35/20* (2019.02)

(56) References Cited

U.S. PATENT DOCUMENTS

| | | | |
|---|---|---|---|
| 6,377,893 | B1 | 4/2002 | Benner |
| 6,512,981 | B1 | 1/2003 | Eisenberg et al. |
| 6,832,162 | B2 | 12/2004 | Floudas et al. |
| 7,158,891 | B2 | 1/2007 | Gautham et al. |
| 2003/0215877 | A1 | 11/2003 | Love et al. |
| 2006/0216688 | A1* | 9/2006 | Maher ............... G01N 33/5076 435/4 |
| 2014/0170239 | A1 | 6/2014 | Schymkowitz et al. |

OTHER PUBLICATIONS

Bates, Paul A. et al., Enhancement of Protein Modeling by Human Intervention, Proteins: Structure, Function, and Genetics, 2001, 39-46, Suppl 5.
Berman, H. M. et al., The Protein Data Bank, Nucleic Acids Res., 2000, 235-242, 28(1).
Bethea, Deidra et al., Mechanisms of self-association of a human monoclonal antibody CNTO607, Protein Engineering Design & Sectetion, 2012, 531-537, 25(10).
Bonneau, Richard et al., Ab Initio Protein Structure Prediction: Progress and Prospects, Annu. Rev. Biophys. Biomol. Struct., 2001, 173-189, 30.
Chothia et al, Canonical Structures for the Hypervariable Regions of Immunoglobins, J. Mol. Biol., 1987, 901-917, 196.
Chothia et al., Conformations of immunoglobin hypervariable regions, Nature, 1989, 877-883, 342.
Eswar, Narayanan et al., Comparative Protein Structure Modeling Using Modeller, Current Protocols in Protein Science, 2001, 5.6.1-5.6.30, Supplement 50.
Ingwall, R. T. et al., Conformational Studies of Poly-L-Alanine in Water, Biopolymers, 1968, 331-368, 6.
Insaidoo, F. et al., Computational modeling: Insights into molecular biophysics to advance and improve biologics purification, 247th American Chemical Society National Meeting, 2014, 33, Abstract 33.
Kabat, The Structural Basis of Antibody Complementarity, Adv. Prot. Chem., 1978, 1-75, 32.
Kabat, Unusual Distributions of Amino Acids in Complementarity-determining (Hypervriable) Segment of Heavy and Light Chains of Immunoglobulins and Their Possible Roles in Specificity of Antibody-combining Sites, J. Biol. Chem., 1977, 6609-6616, 252.
Koehl, Patrice et al., Mean-field minimization methods for biological macromolecules, Curr Opin Struct Biol, 1996, 222-226, 6(2).
Lesk, Arthur M., CASP2: Report on Ab Initio Predictions, Proteins: Structure, Function, and Genetics, 1007, :151-166, Suppl. 1.
Levitt, Michael, Accurate Modeling of Protein Conformation by Automatic Segment Matching, J. Mol. Biol., 1992, 507-533, 226.
Roush, D. et al., Computational Modeling: Insights into Molecular Biophysics to Advance and Improve Biologies Purification, Recovery of Biological Products XVI, 2014, 1, Abstract.
Roush, D. et al., Rationale purification development: Leveraging molecular biophysics to target purification modalities, 249th ACS Meeting, Denver, CO, 2015, 530, Abstract 530.
Schwede, Torsten et al., Swiss-Model: an automated protein, Nucleic Acids Research, 2003, 3381-3385, 31 (13).
Xiang, Zhexin, Advances in Homology Protein Structure Modeling, Curr Protein Pept Sci., 2006, 217-227, 7(3).
Zemla, Arthur et al., Numerical Criteria for the Evaluation of Ab Initio Predictions of Protein Structure, Proteins: Structure, Function, and Genetics, 1997, 140-150, Suppl. 1.
Petukh, Marharyta, et al., The Role of Protonation States in Ligand-Receptor Recognition and Binding, Current Pharmaceutical Design, 2013, 4182-4190, vol. 19, No. 23.
Tarar, Haider Sulaiman, Optimum protein-excipient interactions using molecular docking simulations, Journal of Undergraduate Research, 2014, 69-73, Spring 2014.
Veurink, Marieke, et al., Breaking the Aggregation of the Monoclonal Antibody Bevacizumab (Avastin®) by Dexamethasone Phosphate: Insights from Molecular Modelling and Asymmetrical Flow Field-Flow Fractionation, Pharmaceutical Research, 2013, 1176-1187, vol. 30, No. 4.
Westermaier, Y., et al., Identification of aggregation breakers for bevacizumab (Avastin) self-association through similarity searching and interaction studies, European Journal of Pharmaceutics and Biopharmaceutics, 2013, 773-780, vol. 85, No. 3.
Veurink, Marieke et al., Breaking the Aggregation of the Monoclonal Antibody Bevacizumab (Avastin®) by Dexamethasone Phosphate: Insights from Molecular Modelling and Asymmetrical Flow Field-Flow Fractionation, Pharmaceutical Research, 2013, 1-13, 30(4) Supplemental Material.

* cited by examiner

FIG. 1A  Protein Monomer  $\Delta G_P$

FIG. 1B  Protein-Protein Docking  $\Delta G_{PP}$

FIG. 1C  Protein-Excipient Complex  $\Delta G_{PE}$  $\Delta G_E < -3$ kcal/mole FIG. 1D  Protein-Excipient-Protein Sandwich  $\Delta G_{PEP}$

Simulation of impact of excipient on protein: protein dock energy

Binding Affinities of Amino Acids to Protein-Protein Interaction Sites

FIG.3C

FIG. 4A
Crystal Structure

FIG. 4C
Crystal and Docking Structure Overlay

FIG. 4B
High Energy Crystal Contacts

FIG. 4D
High Energy Docking Contacts

IN SILICO PROCESS FOR SELECTING PROTEIN FORMULATION EXCIPIENTS

CROSS-REFERENCE TO RELATED APPLICATIONS

This application is a § 371 National Phase Application of International Application No. PCT/US2017/020847, filed Mar. 6, 2017, which claims priority from U.S. provisional application 62/307,006 filed Mar. 11, 2016.

BACKGROUND OF THE INVENTION

Lyophilized and liquid formulations of a therapeutic protein represent an increasing percentage of pharmaceutical products that are approved each year. The excipients in such biological products not only need to be suitable for use in an injectable formulation, they must stabilize the protein against degradation that can occur during preparation and storage of the formulated product. While various mechanisms of degradation have been identified, aggregation of protein molecules by protein self-association is probably the most common and yet the least understood mechanism. The formation of protein aggregates in a biological product can result in reduced efficacy and increased risk to elicit an immune response against the therapeutic protein.

The process of selecting formulation excipients that will mitigate aggregation typically involve high-throughput empirical screening of a large number of excipients and other formulation conditions, a process which consumes a significant amount of time and material. As such, there is a need to streamline this empirical process by developing in tools to predict whether a particular protein is prone to aggregation, to identify what regions of the protein are involved in aggregation and which excipients are most likely to mitigate such aggregation if incorporated into a candidate formulation.

SUMMARY OF THE INVENTION

The present invention helps address this need in the formulation art by providing an in silico excipient screening approach. This approach combines computational molecular modeling and molecular dynamics simulations to identify sites on a protein where non-specific self-interaction and interaction of different test excipients may occur, determine the relative binding energies of such interactions, and select one or more test excipients that meet specified interaction criteria for use as candidate excipients in empirical screening studies.

Thus, in one aspect, the invention provides an in silico screening method to identify candidate excipients for reducing aggregation of a protein in a formulation. The method comprises the following steps:
  a) obtaining a three-dimensional (3D) structure of the protein and a 3D structure of at least one test excipient, wherein the 3D protein structure and the 3D excipient structure are at the same level of resolution;
  b) selecting at least one region of the 3D protein structure to probe for potential sites of non-specific inter-molecular interactions between monomers of the protein and between monomers of the protein and at least one molecule of the test excipient;
  c) protonating the selected protein region to a desired pH;
  d) conducting a first probe-protein docking simulation over the entire surface area of the selected protein region, using as a first probe the 3D protein structure, to identify a set of one or more protein-protein docking sites whose docking scores in total equal −3 kcal/mol or lower;
  e) conducting a second probe-protein docking simulation over the entire surface area of the selected protein region, using as a second probe the 3D excipient structure, to identify any excipient-protein docking sites and classifying for further analysis as a putative protein-excipient complex each identified site that has a docking score that is −3 kcal/mol or lower, wherein each of the first and second probe-protein docking simulations may be conducted in either order or simultaneously;
  f) conducting a third probe-protein docking simulation over the entire surface area of each protein-excipient complex classified in step (e), using as a third probe at least one molecule of the 3D protein structure, and at all orientations of the protein, to identify each docking site for the protein on the protein-excipient complex that overlaps with any of the protein-protein docking sites identified in step (d) and classifying each overlapping site as a protein-excipient-protein sandwich; and
  g) selecting the test excipient as a candidate excipient to reduce aggregation of the protein in the formulation if at least one protein-excipient-protein sandwich classified in step (f) has a docking score that represents a lower binding affinity than the docking score for the protein-protein docking site in the sandwich.

In yet another embodiment of the invention, the method further comprises repeating obtaining a 3D structure for a second test excipient that is at the same level of resolution as the protein and repeating steps (d) through (g) using the second excipient 3D structure instead of the first excipient 3D structure.

In a still further embodiment, the method further comprises examining in vitro the ability of the selected candidate excipient(s) to reduce aggregation of the protein in the formulation.

In any of the above embodiments of the invention, the resolution of the 3D structure for each of the protein and the test excipient may be at the atomic level or at an intermediate level. In such embodiments, the 3D structure may be pre-determined (i) computationally by a molecular modeling algorithm or (ii) experimentally by X-ray crystallography, nuclear magnetic resonance or cryo-electron microscopy. In some embodiments, the 3D structure of the protein is pre-determined experimentally and is obtained from a protein structure database, such as the Protein Data Bank (PDB).

In some embodiments where the 3D structure obtained for each of the protein and the test excipient is at the atomic level, the method further comprises conducting, before step (f), a molecular dynamics simulation on each putative protein-excipient complex classified in step (e) and retaining for use in step (f) each protein-excipient complex that has a binding free energy of −3 kcal/mol or lower.

In some embodiments, the protein of interest is a candidate antibody therapeutic and its 3D structure at the atomic level is pre-determined by a computational modeling process that comprises the steps of:
  (a) providing amino acid sequences for framework regions (FR) and complementarity determining regions (CDR) in a set of antibody Fabs for which the 3D structure has been experimentally determined;
  (b) aligning, for a first FR in the candidate antibody and the corresponding FR in each provided Fab, the amino acid sequences to identify each Fab FR that shares at least 85% sequence identity with the candidate antibody FR and selecting the 3D structure of the Fab FR that has the highest sequence identity with the candidate antibody FR for use as the structural model for the first FR (c) repeating step (b) for each FR in the candidate antibody;

(d) aligning, for a first CDR in the candidate antibody and corresponding CDR in each provided Fab, the CDR amino acid sequences and selecting, for use as the structural model for the FR of interest, the 3D structure of the Fab CDR that has about the same length as the candidate antibody CDR and is likely to form a higher ordered structure;

(e) repeating step (d) for each CDR in the candidate antibody;

(f) grafting together the 3D structures of the selected Fab FRs and Fab CDRs and mutating the FR and CDR amino acid sequences in the grafted structure to be the same as in the candidate antibody to derive a Fab structural model of the candidate antibody;

(g) superimposing two copies of the Fab structural model onto the structure of a full length IgG antibody with an Fc of the same isotype as the candidate antibody;

(h) joining the two Fab copies with the Fc using a linker that is modeled to provide the appropriate disulfide bonds and thereby derive a full-length structural model of the candidate antibody;

(i) performing a molecular dynamics simulation on the full-length structural model that packs the side chains and eliminates any clashes in the structure to generate an energy minimized structure of the candidate antibody.

In any of the above embodiments, the method may be performed on an antibody and the first and second probe docking simulations are performed for at least two antibody regions selected from the group consisting of all light chain CDRs, all heavy chain CDRs, each Fab, the Fc region and the entire antibody.

In any of the above embodiments, the formulation may be a liquid formulation.

In any of the above embodiments, the test excipient(s) may be an amino acid.

In other aspects, the invention provides (i) a machine-readable medium for carrying out the method of any of the above embodiments, comprising machine-readable instructions encoded thereon which, when executed by a processor, cause a machine having or linked to the processor to execute the method and (ii) a computer system comprising this machine-readable medium and a user interface capable of receiving the 3D structures of the protein and excipients and user selected criteria applied in one or more steps of the method.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 is a graphical illustration of performing several steps in an embodiment of the in silico method of the invention showing: the 3D structure of an antibody as a monomer in its native state (Panel A); a result of the first probe-protein docking simulation that identified an intermolecular docking site between a CDR of one antibody molecule and the framework region of a another molecule of the antibody (Panel B); a result of the second probe-protein docking simulation that identified an excipient docking site at the same antibody CDR and has been classified as a putative protein-excipient complex (Panel C); and a result of the third probe-protein docking simulation that identified a docking site where a protein-excipient-protein sandwich could form with the potential to disrupt protein self-association (Panel D).

FIG. 2 illustrates operability of the in silico screening method of the invention using CNT0607, a mAb with known areas of self-association (Bethea, D. et al., *Protein Engineering Design & Sectetion*, Vol 25(10) 2012), showing: (A) a ribbon diagram of a this mAb self-associating with a space filled model of the same mAb; (B) a ribbon diagram of the Fab of this mAb showing a CDR and an excipient interaction site in the same region as the CDR, with the excipient shown as a ball and stick structure in yellow); (C) an enlarged view of the excipient-CDR interaction site shown in (B); (D) ribbon diagram of a complex of two CNT0607 molecules in the same conformation as depicted in panel (A), with the interaction (i.e., docking) site including a CDR on the left molecule and a framework region (FR) on the right molecule; (E) a ribbon diagram showing the same protein-protein complex shown in panel (D) and mesh surfaces for twenty amino acids (orange color) and their interaction sites on the CDR in the left molecule; and (F) an enlarged view of the CDR and amino acid mesh surfaces shown in panel (E).

FIG. 4 illustrates the comparison of high affinity protein-protein interactions for CNT0607 using an experimentally determined 3D crystal structure (panels (A) and (B)) and a computationally determined 3D structure model (panels C and D), showing: (A) interaction of two CNT0607 molecules at the CDR-FR interaction site; (B) an enlarged view of the CDR-FR interaction site with the highest energy contacts between two FR lysine residues in one molecule and two CDR aspartic acid residues in the other molecule; (C) the same orientation of two interacting CNTO607 molecules in which the highest docking score pose has been superimposed on the crystal structure orientation and (D) the highest energy docking contacts of the same CDR and FR amino acid residues as observed using the experimentally determined crystal structure.

DETAILED DESCRIPTION OF THE INVENTION

As used herein, including the appended claims, the singular forms of words such as "a," "an," and "the" include their corresponding plural references unless the context clearly dictates otherwise.

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

All references cited herein are incorporated herein by reference to the same extent as if each individual publication, patent, or published patent application was specifically and individually indicated to be incorporated by reference.

The present invention may be used in screening test excipients for use in formulating any type of protein for which a model of its three-dimensional structure is available or may be generated. As used herein, the term protein means any sequence of at least two amino acids (also referred to herein as "amino acid residues" or "residues") joined together by peptide bonds between carboxyl and amino groups of adjacent amino acids, regardless of length, post-translation modification, chemical modification of function. Typically, the protein is of sufficient length to fold into a three-dimensional (3D) structure. Thus, the terms "protein", "polypeptide", and "peptide" are used interchangeably herein, unless otherwise apparent from the context in which the term is used. In particular, it is envisioned that the in silico screening method of the invention may be applied to cytokines, chemokines, enzymes, fusion proteins, hormones, immunoglobulins, antibodies, monoclonal antibodies (mAbs), and antigen binding fragments of mAbs, and antigens among other types of proteins intended for therapeutic use. The protein may be a naturally-occurring or recombinantly-produced protein, or may be chemically synthesized. In some embodiments, the protein may be chemically conjugated to a polymer (e.g., a pegylated protein) or to a therapeutically active moiety (e.g., an antibody-drug conjugate). The protein may incorporate unusual or unnatural amino acids.

In some embodiments, the protein to be formulated is an antibody or immunoglobulin. As used herein, the term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids that is primarily responsible for antigen recognition. The carboxy-terminal portion of the heavy chain may define a constant region that is primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), which are located within relatively conserved framework regions (FR). The CDRs are usually aligned by the framework regions, enabling binding to a specific epitope on an antigen. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196: 901-917 or Chothia, et al., (1989) Nature 342:878-883.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', $F(ab')_2$, and Fv fragments; diabodies; linear antibodies; single-chain antibody molecules, e.g., sc-Fv; nanobodies and multispecific antibodies formed from antibody fragments.

The in silico screening method of the invention is performed using a 3D structure of the protein, i.e., a three-dimensional model that represents the protein's secondary, tertiary, and/or quaternary structure. Models of 3D structures useful in the methods of the invention include X-ray crystal structures, NMR structures, theoretical protein structures, structures created from homology modeling, Protein Tomography models, and atomistic models built from electron microscopic studies. Typically, a 3D structure will provide coordinates for the protein atoms in three-dimensional space, thus showing the protein folds and amino acid residue positions.

In some embodiments, the protein structure used in the screening method of the invention was experimentally determined by X-ray crystallography, and may be determined de novo or obtained from a protein structure database. A variety of databases that contain 3D protein structures are publicly available. One well-known database is the Protein Data Bank archive (PDB), which is managed by the Worldwide PDB organization, whose members offer various tools for searching visualizing and analyzing PDB data, including the Research Collaboratory for Structural Bioinformatics Protein Data Bank (RCSB PDB) (described in Berman, H. M et al., Nucleic Acids Res. 28(1); 235-42 (2000), accessed at ww.rcsb.org/pdb/), Biological Magnetic Resonance Bank (BMRB), Protein Data Bank in Europe (PDBe), and Protein Data Bank Japan (PDBj). Another database that contains 3D structures for various proteins is the Research Consortium for Structural Bioinformatics (RSCB).

In other embodiments, the protein structure used in the screening method of the invention has been computationally determined by a molecular modeling algorithm. Such algorithms typically employ homology modeling, which involves comparing a protein's primary sequence to the known three dimensional structure of a similar protein.

Homology modeling is well known in the art. See, e.g., Xiang, *Curr Protein Pept Sci.* 2006 June; 7(3):217-227. For antibodies, the structure of antibody variable regions can be obtained accurately using the canonical structures method (Chothia C and Lesk A M, *J. Mol. Biol.* 1987, 196, 901; Chothia C et al., Nature 1989, 342, 877).

A computationally determined 3D structure of the protein may be obtained using commercially available software that employs homology modeling, e.g., MODELLER (Eswar, et al., *Comparative Protein Structure Modeling With MODELLER.* Current Protocols in Bioinformatics, John Wiley & Sons, Inc., Supplement 15, 5.6.1-5.6.30, 200), SEGMOD/ENCAD (Levitt M. *J Mol Biol* 1992; 226:507-533), SWISS-MODEL (Schwede T, Kopp J, Guex N, Peitsch M C. *Nucleic Acids Research* 2003; 31:3381-3385), 3D-JIGSAW (Bates et al., *Proteins: Structure, Function and Genetics*, Suppl 2001; 5:39-46), NEST (Xiang, *Curr Protein Pept Sci.* 2006 June; 7(3): 217-227), and BUILDER (Koehl and Delarue, *Curr Opin Struct Biol* 1996; 6(2):222-226). In some embodiments, the 3D structure was computationally generated using the Protein Modeling and Bioinformatics applications in the Molecular Operating Environment (MOE), which is a comprehensive software system available from Chemical Computing Group Inc. (CCG) (Montreal, Quebec, Canada).

In some embodiments, homology modeling may be used to assemble full proteins from known structure fragments, such as when an antibody Fab fragment is modeled onto an Fc fragment, or when a Fab fragment is created as a theoretical protein structure and modeled onto a Fc fragment crystal structure. A skilled artisan will understand that various possibilities exist. In one particular embodiment a Fab fragment may be modeled onto various antibody Fc structures of different classes or isotypes.

An ab initio model of the protein 3D structure may also be used in the screening method of the present invention. An "ab initio structure" is created directly from the protein primary sequence by simulating the protein folding process using various equations derived from physical chemistry (Bonneau and Baker, *Annual Review of Biophysics and Biomolecular Structure,* 2001, Vol. 30, Pages 173-189; Lesk, *Proteins* 1997, 1:151-166. Suppl; Zemla, et al. *Proteins* 1997, 1:140-150.Suppl; Ingwall, et al. *Biopolymers* 1968; 6:331-368; and U.S. Pat. Nos. 6,832,162; 5,878,373; 5,436,850; 6,512,981; 7,158,891; 6,377,893; and U.S. patent application Ser. Nos. 9/788,006; 11/890,863; and Ser. No. 10/113,219).

In some embodiments, the 3D structure of the protein that has been obtained experimentally or computationally is processed before applying the screening method of the present invention. For example, the obtained protein structure may be put through a molecular dynamics simulation to allow the protein side chains to reach a more natural conformation, or the structure may be allowed to interact with solvent, e.g., water, in a molecular dynamics simulation. This processing is not limited to molecular dynamics simulation and can be accomplished using any art-recognized means to determine movement of a protein in a solution state (e.g., for an intended liquid formulation) or in a solid state (e.g., for an intended lyophilized formulation). An exemplary alternative simulation technique is Monte Carlo simulation. Simulations can be performed using simulation packages or any other acceptable computing means. In certain embodiments, simulations to search, probe or sample protein conformational space can be performed on a structural model to determine movement of the protein.

The in silico screening method of the invention may be used to screen a variety of test excipients that are typically examined in formulation screening studies conducted in vitro. The test excipients may be chosen from categories of stabilizing excipients that are commonly added to therapeutic protein formulations to stabilize the protein against aggregation, which include: buffering agents; amino acids and modifications thereof; salts; sugars and carbohydrates; surfactants; polymers; and chelators and antioxidants. Choosing test excipients to screen for a particular protein will typically include consideration of whether the desired formulation is to be a liquid or lyophilized formulation and what is known about the properties of the protein to be formulated.

Representative examples of buffering agents include citrate, acetate, histidine, phosphate, and Tris.

Representative examples of amino acids that have been used in protein formulations include histidine, arginine, glycine, proline, lysine and methionine. In some embodiments of the invention, all 20 amino acids are employed as test excipients.

Representative examples of salts include sodium chloride, potassium chloride, and sodium sulfate.

Representative examples of sugars and carbohydrates include sucrose, trehalose, mannitol, sorbitol, glucose and lactose.

Representative examples of surfactants include polysorbate 20 and polysorbate 80, and alkylsaccharides.

Representative examples of polymers include dextran and polyethylene glycol.

Representative examples of chelators and anti-oxidants include EDTA, DTPA, methionine, histidine, and ethanol.

In some embodiments, the test excipients will be those that have been classified by the FDA as "generally regarded as safe" (GRAS). A database of GRAS excipients is available online at the FDA website (www.fda.gov/Food/FoodIngredientsPackaging/GenerallyRecognizedasSafeGRAS/GRASSubstancesSCOGSDatabase/default.htm).

Other potential test excipients to be screened in the method of the invention may be selected from the FDA Inactive Ingredient database of pharmaceutical excipients found in FDA approved drugs, including parenteral products, which is also accessible on the FDA website Inactive Ingredient Search for Approved Drug Products (www.accessdata.fda.gov/scripts/cder/iig/index.cfm).

Once one or more test excipients to be screened are chosen, 3D structures need to be obtained for the test excipients. The 3D structures should be at the same level of resolution as the protein 3D structure. Excipient structures may be obtained using resources and tools knows to the skilled artisan, including the scientific literature, structure databases or computationally generated using modeling software that employs energy minimization, molecular dynamics and conformation search.

Once the 3D structure for the protein has been obtained and any desired conformational processing is performed, the 3D structure is protonated to a desired pH. The desired pH will typically be within a range that is dictated by the stability of the molecule under various formulation conditions, and which may be estimated from pI calculations. In particular, it is generally thought that the pH of a protein formulation should be moved away from the pI of the protein. In some embodiments, the 3D structure of the test excipient is protonated to the same pH as used for the protein structure.

To probe the protein for potential sites of intermolecular self-association and excipient interactions, two different types of probe-protein docking simulations are conducted, either simultaneously or sequentially, over the entire surface area of at least one region of interest on the protonated 3D protein structure. Molecular docking simulation software programs are well-known in the art, and include, e.g, the protein docking approach described in Chemical Computing Group MOE 2015 documentation.

The choice of which protein region(s) to probe will typically depend on the size and type of protein, as well as the amount of computing time required to conduct the simulations. The selected region may include, for example, the part of the protein that is primarily responsible for its biological activity, e.g., the specific binding site for a different protein. For example, if the protein is a receptor, then the selected region might comprise the binding site for the biological ligand for that receptor. Similarly, if the protein is a mAb, the selected region may comprise any of the 6 CDRs. In some embodiments, the entire surface area of the protein 3D structure is probed.

In one type of the probe-protein docking simulations, the probe is the protonated 3D protein structure. In some embodiments, the protein-protein docking simulation uses a combination of a quick configuration space sweep using Fast-Fourier Transforms (FFTs) to identify grid-based interactions between two molecules of the protein. This is followed by fast rigid-body interaction energy minimization of the top configurations using the Truncated Newton approach along with a residue based coarse-grained (CG) representation that include the following energy components (van der Waals, electrostatic, and solvation via the Generalized Born Volume interaction (GB/VI) formalism). Since all docking studies use static structures, the resulting improvements in biophysical properties are applicable to both liquid and lyophilized formulation.

The docking scores (e.g., binding affinity) for each site of protein-protein interaction are determined and ranked. A protein is classified as having a potential for intermolecular self-association (e.g., aggregation) if there is at least one set of one or more docking sites for which the sum of the individual docking scores is −3 kcal/mol or lower. As will be understood by the skilled artisan, binding affinity increases as a docking score ($\Delta G$) gets more negative. Thus, the likelihood of a protein being susceptible to inter-molecular association increases as the summed docking scores for protein-protein docking sites, which are identified in the docking simulation, become more negative. If the docking simulation for a selected protein region does not generate a set of protein-protein docking sites that satisfy the docking score requirement, then the user may choose to repeat the simulation over the surface area of a different region or the entirety of the protein 3D structure.

In the other type of probe-protein docking simulation, the probe is the 3D excipient structure, which if applicable, is protonated to the same pH as used for the protein structure. In some embodiments, models of amino acid excipients may be created using SMILES (Simplified molecular-input line-entry system) code, built using builder module in Chemical Computing Group (CCG) Molecular Operating Environment (MOE) or alternatively with ChemDraw, which was then imported into the CCG MOE. Subsequently, the amino acid structures may be minimized and/or protonated to achieve the conditions required to support protein-excipient docking simulations.

In some embodiments, the excipient-protein docking starts with a conformational analysis of the excipient, followed by placement of different conformations of the excipient on the selected region of the protein (e.g., poses) and then calculating an initial scoring of the interaction energy based on the poses. The initial scoring is further refined using either explicit mechanics force field method or a grid-based energetics method. The final docking score is then calculated using any of already established scoring schemes. Top scoring poses are screened to remove duplicate poses. Any individual excipient-protein docking site that has a docking score of −3 kcal/mol or lower (i.e., more negative) is classified as a putative protein-excipient complex. If an excipient fails to dock on the protein with a docking score that meets this requirement, then the user may choose to perform the probe-protein docking simulation with another excipient. It is contemplated that the results of conducting multiple probe-protein simulations using different individual excipients may be combined to identify docking sites where at least two different excipients may interact. The user may evaluate the relative docking scores to predict whether including both excipients in the formulation could be beneficial or detrimental in terms of reducing aggregation.

If the first two docking simulations generate (i) at least one set of protein-protein docking sites that meet the docking score requirement stated above (total of individual scores ≤−3 kcal/mol) and (ii) at least one putative protein-excipient complex, then a third type of probe-protein simulation is performed. This simulation is performed over the entire surface area of each protein-excipient complex using as the probe at least one molecule of the 3D protein structure. All orientations of the protein structure are evaluated in the docking simulation. The goal of this simulation is to identify any docking sites for the protein on the protein-excipient complex that overlap with any protein-protein docking site that met the docking score requirements. As used herein, the two different types of docking sites are deemed to be overlapping if protein binding to the protein-excipient complex is within a 4 angstrom radius of the perimeter defined by the protein-protein docking site. Such overlapping sites are classified as a protein-excipient-protein sandwich.

In some embodiments, any or all of protein-excipient, protein-protein or protein-excipient-protein docking simulations can employ counterions, water, and buffer components.

For each protein-excipient-protein sandwich that is identified, the docking score for the entire sandwich ($\Delta G_{PEP}$) is compared to the docking score for the protein-protein docking site in that sandwich ($\Delta G_{PP}$). If at least one sandwich has a $\Delta G_{PEP}$ that is less negative than $\Delta G_{PP}$ (i.e., the presence of the excipient in the sandwich reduced the protein-protein binding affinity), then the test excipient is selected as a candidate excipient for use in the formulation. Typically, the difference between $\Delta G_{PEP}$ and $\Delta G_{PP}$ should be at least 3 kcal/mol, and preferably at least any of 5, 10, 15, 20, 25 or 30 kcal/mol. If no protein-excipient-protein sandwiches meet this requirement (e.g., $\Delta G_{PP}-\Delta G_{PEP}$ is >-3 kcal/mol) then the user may choose to repeat the second and third types of probe-protein simulations using a different excipient.

In some embodiments, the ability of each candidate excipient to reduce aggregation of the protein is examined by conducting appropriate in vitro experiments that are designed to assess protein aggregation and preferably protein stability.

Example 1

This example illustrates the thermodynamic principles of various docking interactions that are evaluated in the screening method of the invention: protein-protein docking, excipient-protein docking and protein-excipient-protein (sandwich) docking.

Example 2

To demonstrate the utility of the in silico screening method of the invention to identify sites of intermolecular protein interactions as well as screen test excipients that may reduce such interactions, four different mAbs were used as model proteins and 20 amino acids were used as test excipients. The CNTO607 mAb was used as a model of a protein for which the 3D crystal structure was publicly available and for which significant aggregation problems had been identified (Bethea et al., supra). The other model proteins were three mAbs whose 3D structures had not been experimentally determined and whose propensity for self-association was unknown. The approach was a direct application of probe-protein docking simulations to determine protein-protein docking sites, protein-excipient docking sites and relative docking scores.

Excipient Structures

The specific excipients evaluated in this assessment were the 20 standard amino acids (Histidine, Alanine, Isoleucine, Arginine, Leucine, Asparagine, Lysine, Aspartic acid, Methionine Cysteine, Phenylalanine, Glutamic acid, Threonine, Glutamine, Tryptophan, Glycine, Valine, Proline, Serine, Tyrosine). Structural models of these amino acids were created using SMILES (Simplified molecular-input line-entry system) code, built using builder module in MOE or alternatively with ChemDraw, which were then imported into Chemical Computing Group (CCG) Molecular Operating Environment (MOE). Subsequently, the amino acid structures were minimized and/or protonated to achieve the conditions required to support protein-excipient docking simulations.

Protein Structures

The 3D structure for CNT0607 was obtained from RCSB (Research Consortium for Structural Bioinformatics) in pdb format (reference file ID 3G6A). Parameterization of this mAb was achieved using AMBER 10 EHT. The structure was subsequently prepared for docking by fixing any missing structure elements, and energy minimization (to a gradient RMS of 0.1 kcal/mol/Å$^2$) to remove steric clashes. For antibodies for which no experimentally determined crystal structure was available (MAB 1, 2, and 3), homology modeling was used to computationally determine the antibody structure.

Protein-Excipient Docking

Amino acid test excipients were docked with a model protein utilizing the following approach. Direct application of excipient docking to determine sites of interaction and relative docking scores (interaction energy) for excipients. Docking was performed using the protein-protein docking approach described in Chemical Computing Group MOE 2015 documentation.

Specific sequence of events included 1) placement which generates poses form a structure library, 2) placement scoring (utilizing Triangle Matcher and scored with London AG), 3) refinement to minimize structures (using Rigid Receptor and scored by GBVI/WSA AG), and 4) final scoring which eliminates duplicate poses.

Highest docking score/binding sites were then identified by rank ordering the docking scores. The highest affinity sites were then interrogated via use of molecular dynamics simulation (~60 ns) to validate protein-excipient interaction and to confirm that the excipient did not dissociate during the simulation.

The docking was repeated for multiple excipients with each model protein. The highest binding affinities for the CNT0607 as the model protein and the 20 amino acids are presented in FIG. 3, panel B. All 20 AA had protein-excipient docking scores ($\Delta G_{PE}$) of −3 kcal/mol or lower and hence could be considered as putative protein-excipient complexes for further analysis. An example of protein-excipient docking is present in FIG. 2, panels B and C. Surface rendering of the interaction sites for all twenty amino acids is presented in FIG. 2, panels E and F, and in FIG. 3, panel C and these sites correspond to the interaction energies plotted in FIG. 3, panel B.

Protein-Protein Docking

Interaction sites for protein intermolecular self-association are illustrated in FIG. 2. The docking algorithm (designated as protein-protein docking in Chemical Computing Group MOE 2015 package) was employed for this example. Details of the algorithm include definition of the receptor site and ligand site, creating coarse grain rigid-body representation of structures, creating grid based representation of receptor field, generating a set of rotations for the ligand, calculating grid-based energy for all translations using FFT convolutions, filter conformation followed by minimization of the poses, additional minimization of the poses to account for solvation free-energy using GBVI and final ranking according to energy.

Figure 1A:
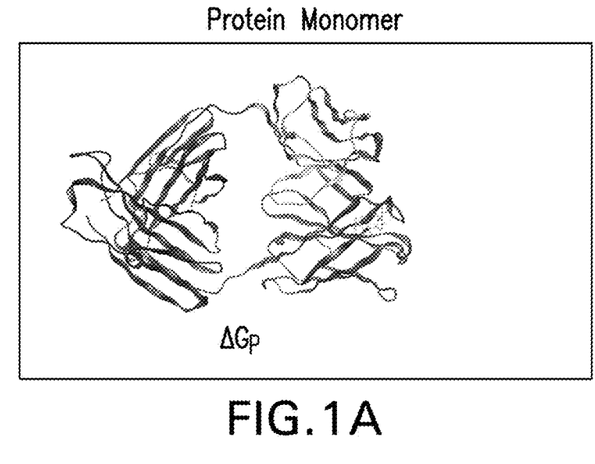
Figure 1B:
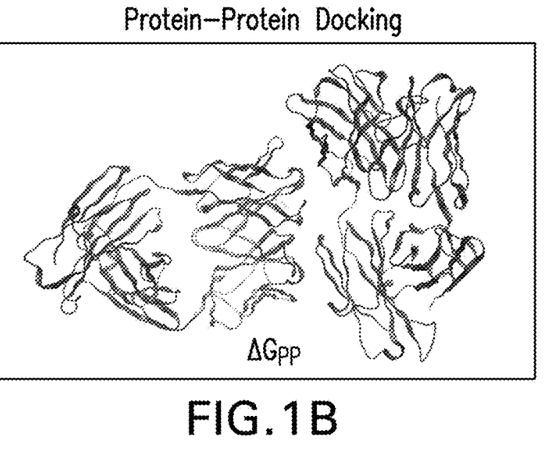
Figure 1C:
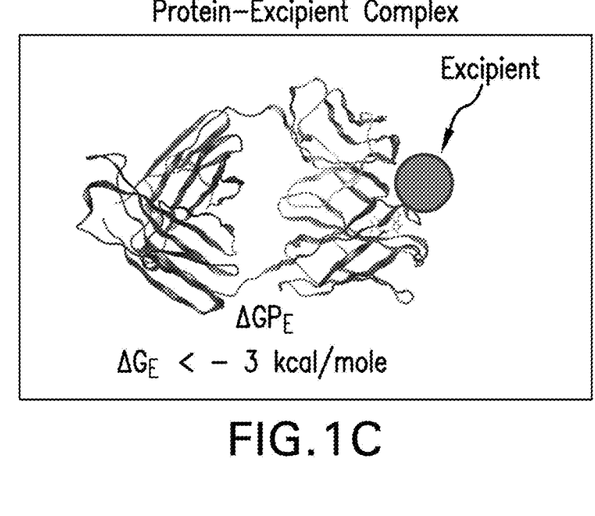
Figure 1D:
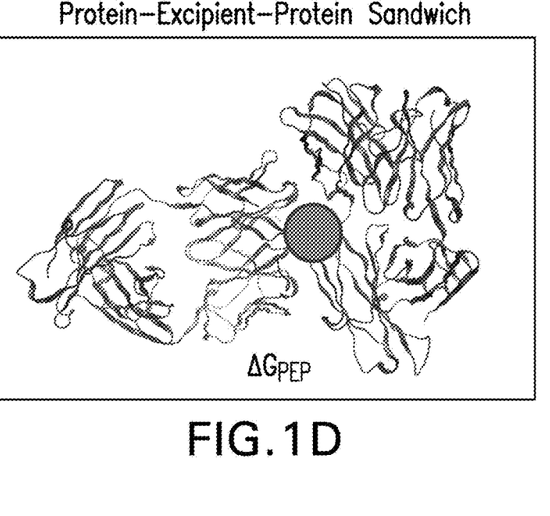
Figure 2A:
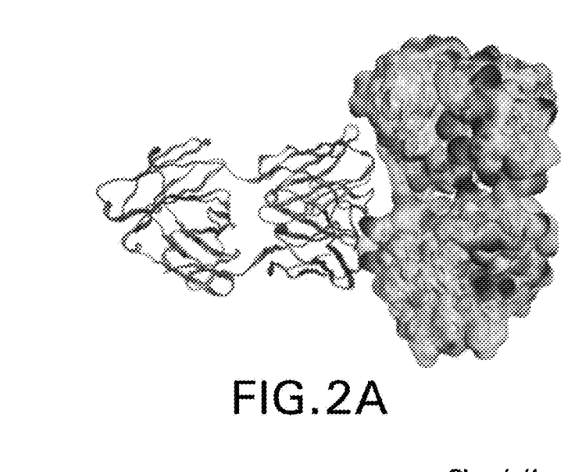
Figure 2B:
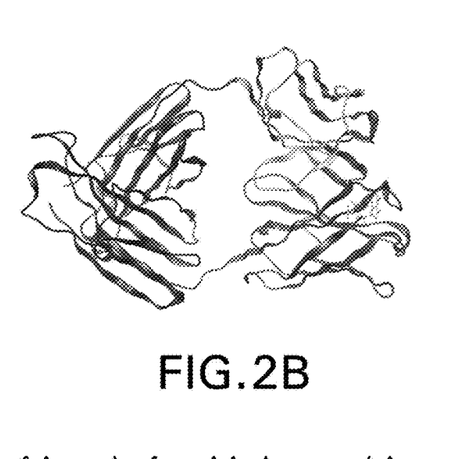
Figure 2C:
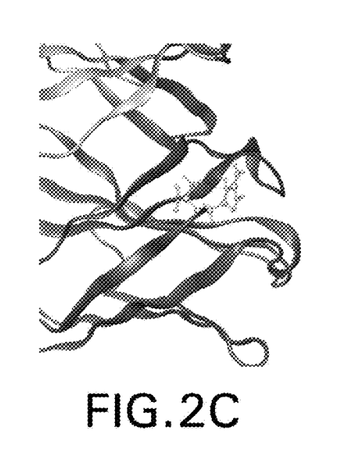
Figure 2D:
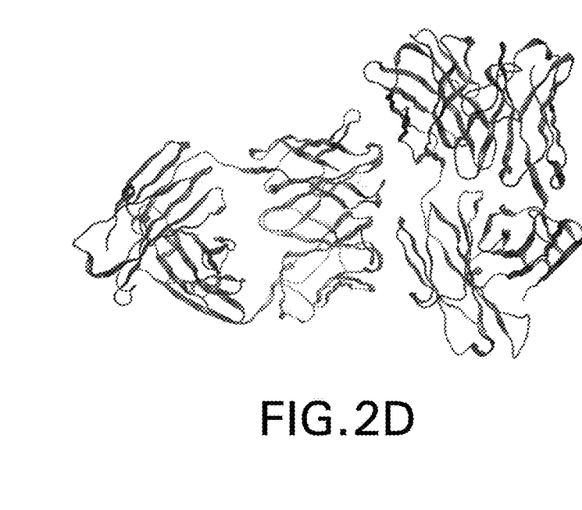
Figure 2E:
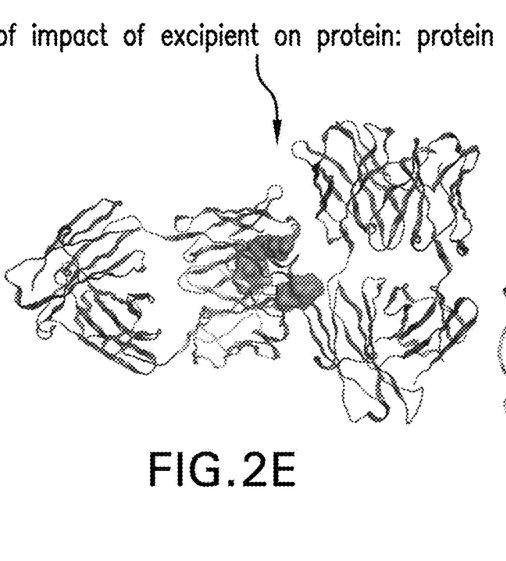
Figure 2F:
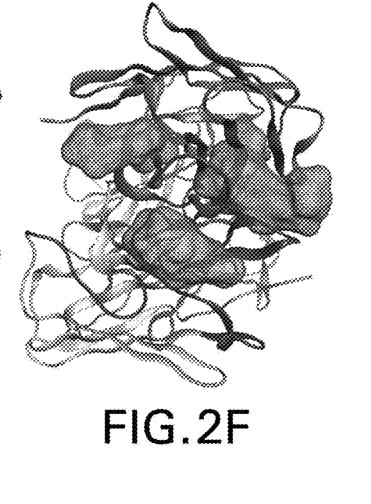
Figure 3A:
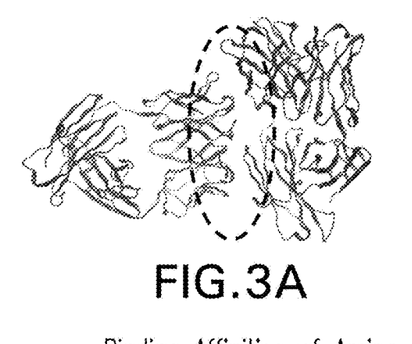
FIG. 3 illustrates screening of 20 amino acids as test excipients for reducing aggregation of CNT0607 showing: (A) the protein-protein complex from panel (D) of FIG. 2, with the dashed black circle indicating the selected region for analysis that includes the CDR-FR interaction site; (B) a graph of the binding affinities (i.e., docking scores) for 20 amino acids in the selected region; and (C) a surface rendering of the CDR-FR interaction site for the 20 amino acids that corresponds to the binding affinities shown in panel (B).
Figure 3B:
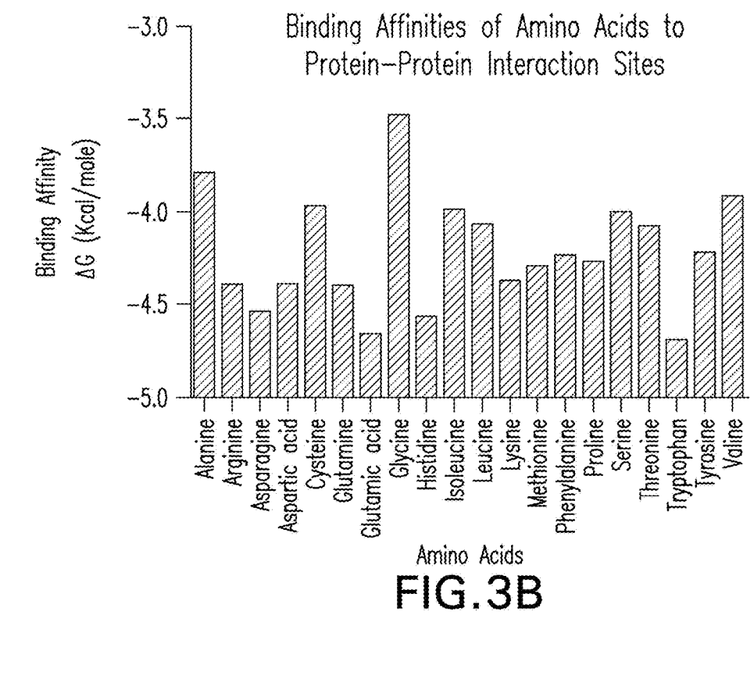
Figure 3C:
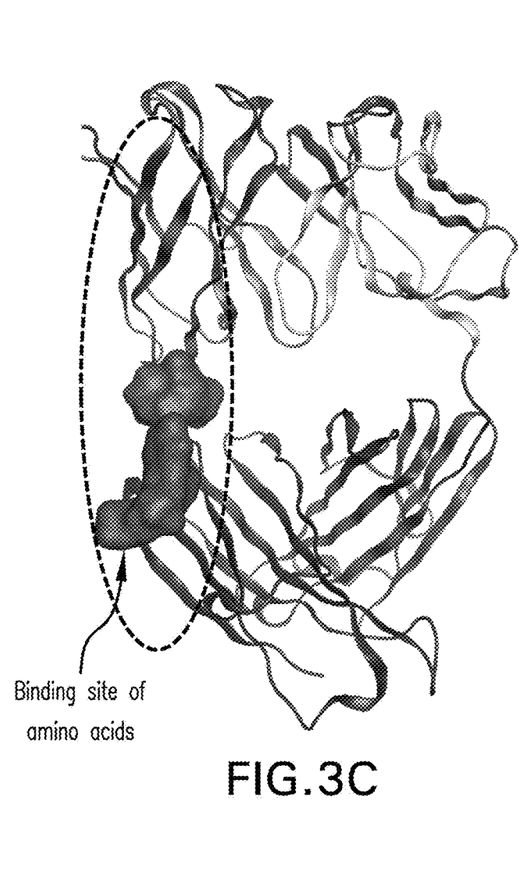
Figure 4A:
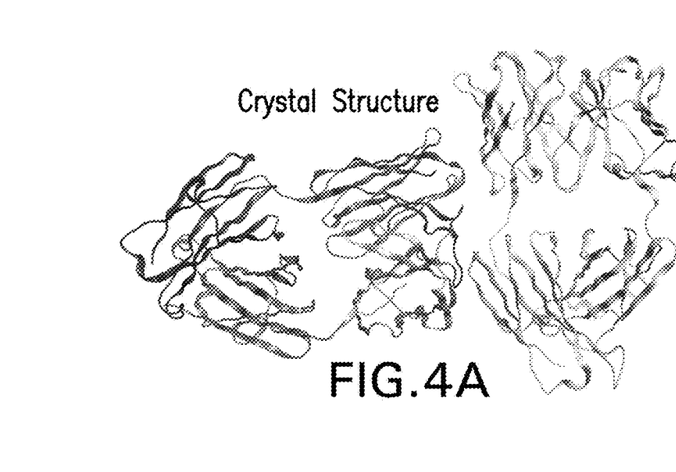
Figure 4B:
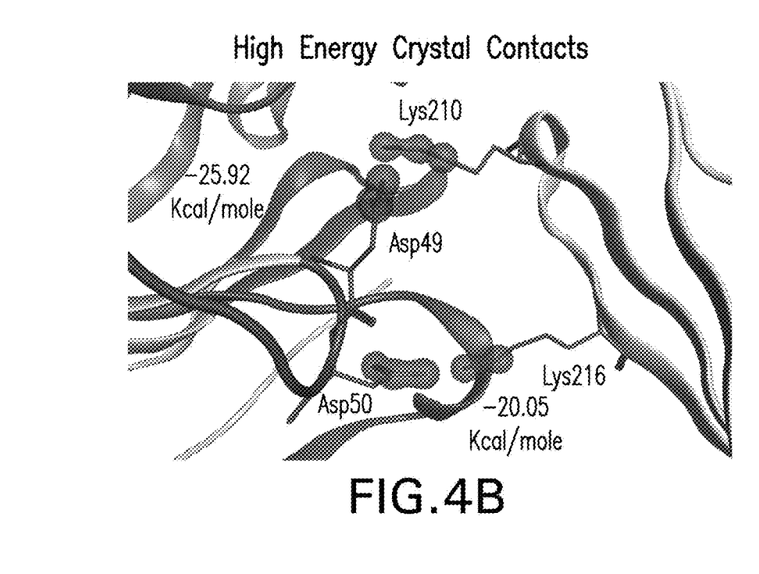
Figure 4C:
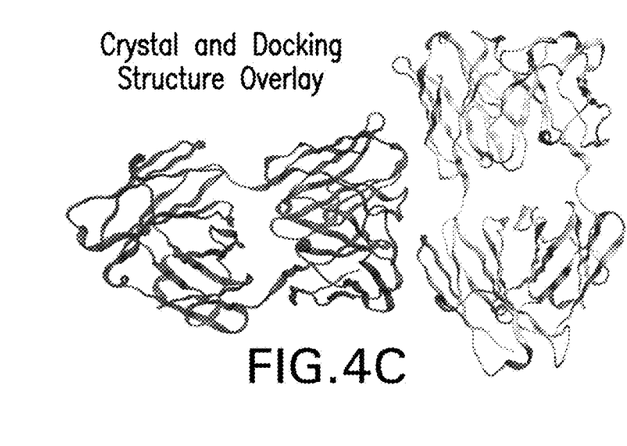
Figure 4D:
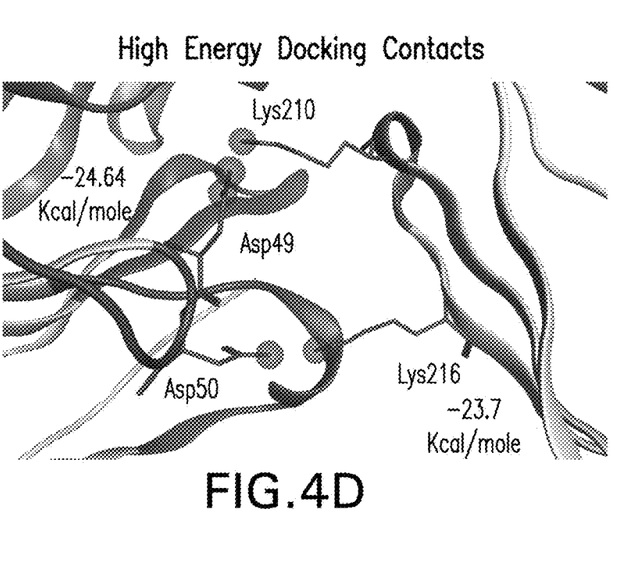

The crystal structure of the protein-protein interaction for CNTO607 is presented in FIG. 2, panels A and D, in FIG. 3, panel A, and in FIG. 4, panel A. Using the crystal structure as a reference, protein-protein docking was performed using the MOE protocol and the highest docking score structure was compare to the original crystal structure. FIG. 4, panel C shows a ribbon diagram of the crystal structure in blue overlaid with the docking pose in red. The two structures look very similar and evaluation of the highest interaction sites reveal that both structures employ a conserved set of residues to achieve this interaction between a CDR and the framework region (FIG. 4, panels B and D). The final calculated interaction energies and orientation are slightly different but are consistent with crystallographically determined contacts. Thus, the highest energy contacts are conserved between crystal structure (C) and modeling results (D).

Protein-Excipient-Protein Docking

Figure 5:
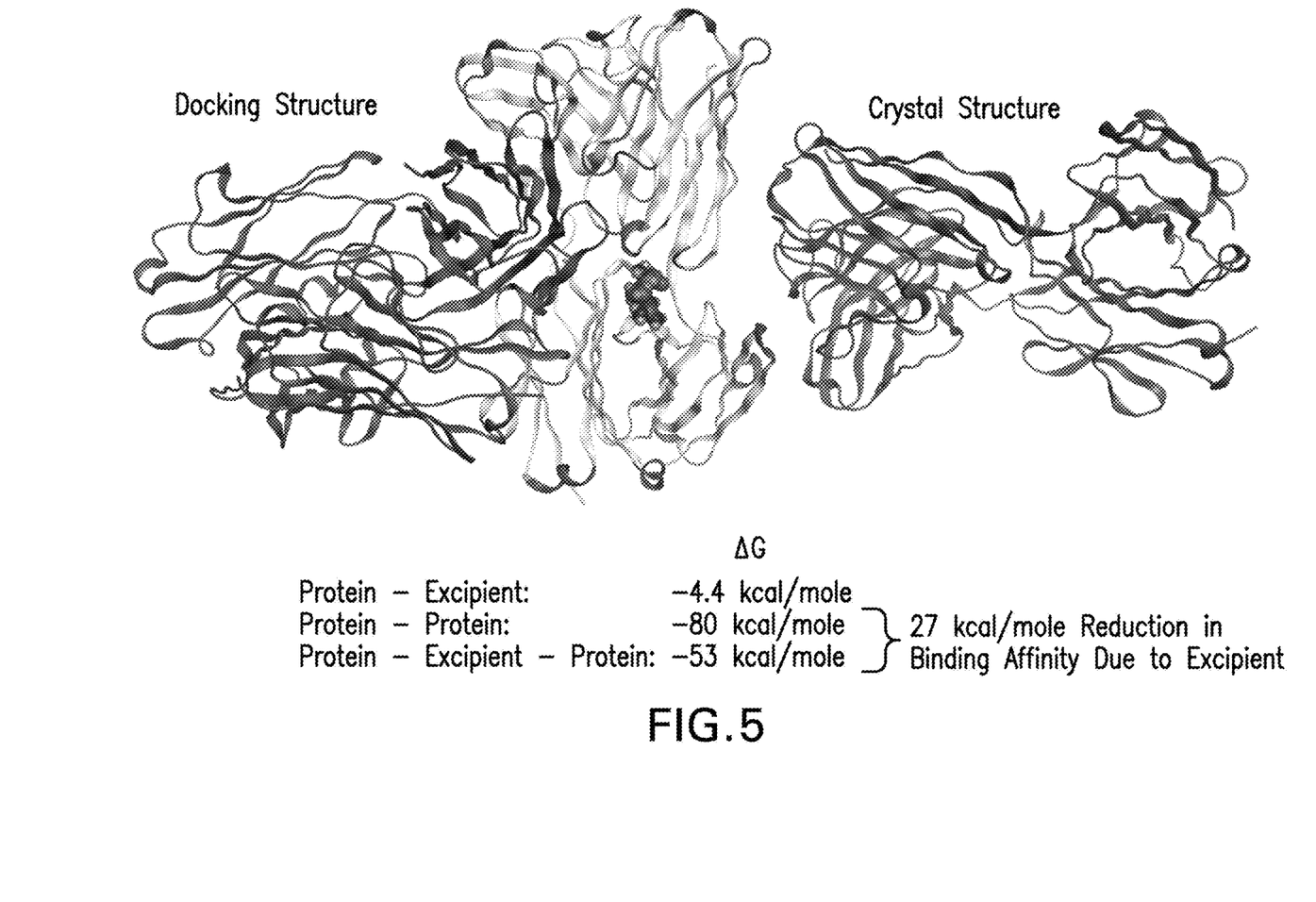
FIG. 5 illustrates the potential of an excipient-protein interaction (i.e., docking) to impact protein-protein interaction (i.e., docking) via binding of the excipient to the protein-protein docking site to generate a protein-excipient-protein sandwich, with protein-excipient-protein docking for a computationally determined structure (shown in red pose) compared to crystallographic protein-protein interaction (depicted in blue ribbon diagram) and the reduction in the binding affinity (i.e., docking score) that is created by the formation of a protein-excipient-protein sandwich.

Using the highest affinity docking score site from the protein-excipient docking simulation a protein-excipient-protein docking simulation was performed to evaluate the impact of amino acid excipients on disrupting the original protein-protein docking conformation and the crystallographic conformation as depicted in FIG. 4. Compared to the original orientation of CNTO607 self-association shown in blue, the highest docking pose adopted a conformation very different from what has been observed in the initial protein-protein docking simulation and was confirmed experimentally (FIG. 5).

Application to Model Antibodies with Unknown Self-Association Properties

Figure 6:
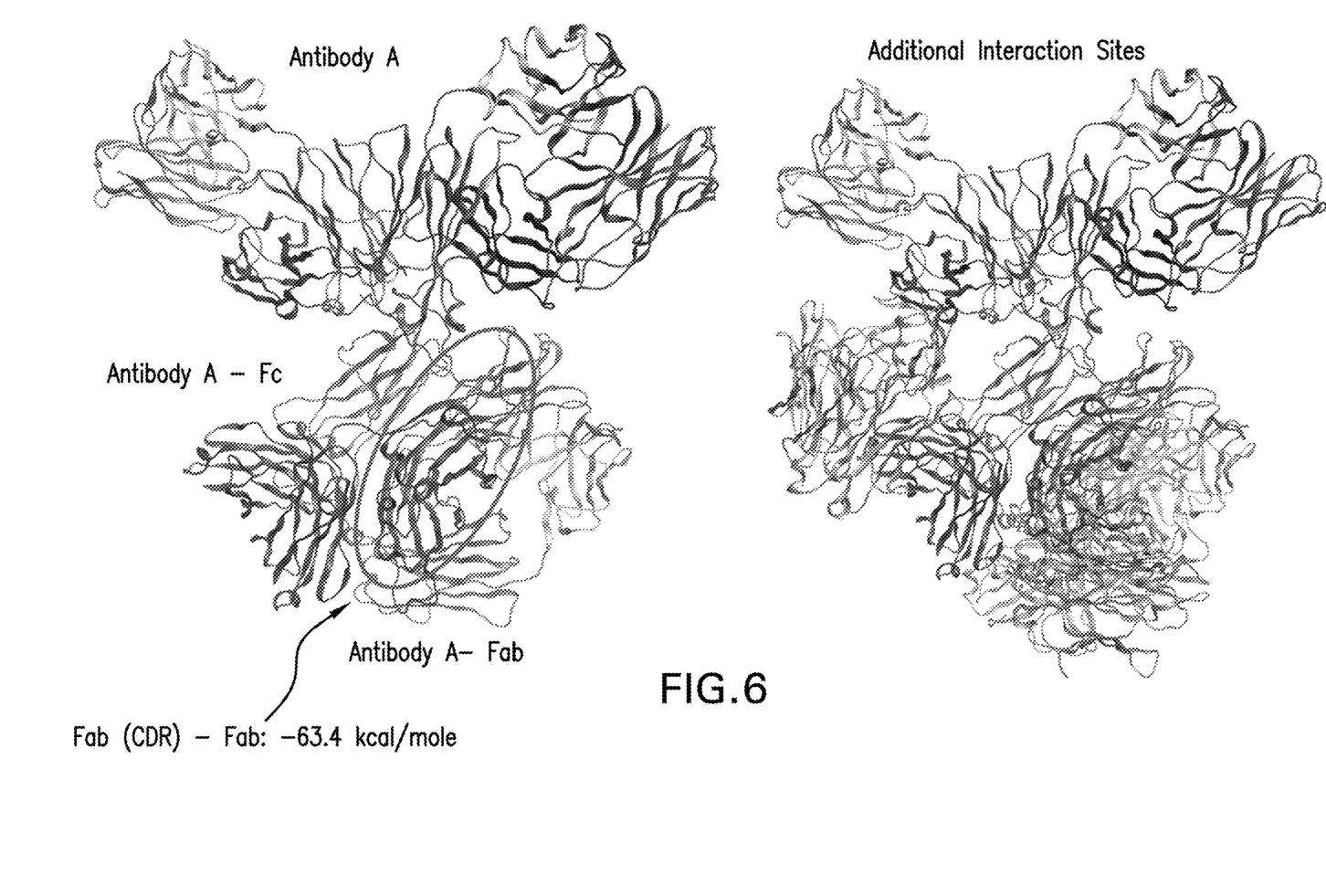
FIG. 6 illustrates the detection of intermolecular association between two molecules of a mAb that was not previously known to self-associate, showing in the left panel an interacting region between the Fc region of the full antibody and a CDR for the Fab of the antibody that had the highest docking score (depicted with red circle) and showing in the right panel additional interaction sites between the full-length antibody and the Fab.
Figure 7:
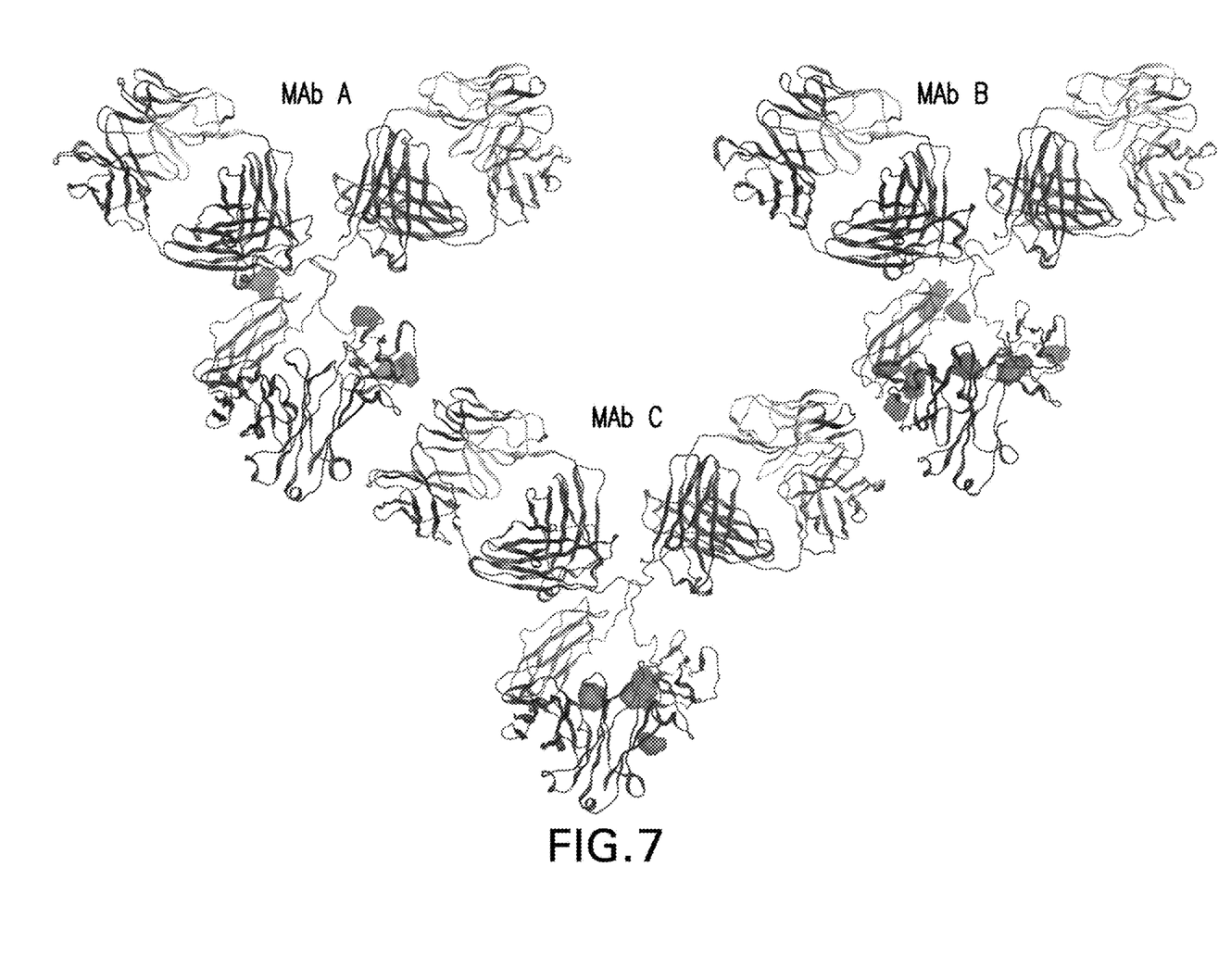
FIG. 7 illustrates protein-excipient docking sites for three different mAbs that met a docking score requirement of −3 to −5 kcal/mol and were identified by conducting a probe-protein docking simulation over the entire surface area of the 3D structure for each mAb using as the probe one of twenty amino acids, with red meshes identifying the sites where amino acid excipients interacted with Mab A (13 of the 20 amino acids), Mab B (all 20 amino acids) and Mab C (all 20 amino acids).

Following the same algorithm as described above, separate protein-protein docking and protein-excipient docking simulations were performed. The protein-protein docking defined the Fc region of the protein as the receptor site and the CDR region of the Fab as the ligand. Following the same algorithm, a site of interaction between a CDR on a Fab molecule and a framework region on the full-length mAb was identified (FIG. 6, left panel). The highest protein-protein docking score utilized a tangential interaction of the CDR and partial framework region overlap as depicted in FIG. 6. This indicates that the Fc region of this mAb is not involved in intermolecular self-association with the DCR. Further, the region of overlap coincides with the region of the mAb where some of the amino acid excipients interact as determined by protein-excipient docking simulation (FIG. 7, panel A). Interestingly, putative excipient protein-excipient complexes were identified for only 13 of the 20 amino acids (R, N, D, Q, E, H, I, L, K, M, F, W, and Y) with Mab A, while all 20 amino acids produced putative excipient protein-excipient complexes for Mab B and Mab C.

We claim:

1. A method of in silico screening of test excipients to select candidate excipients for reducing aggregation of a protein in a formulation, comprising the steps of:
   a) obtaining a three-dimensional (3D) structure of the protein and a 3D structure of at least one test excipient, wherein the 3D protein structure and the 3D excipient structure are at the same level of resolution, wherein the resolution is at the atomic level and pre-determined computationally by a molecular modeling algorithm or experimentally by X-ray crystallography, nuclear magnetic resonance or cryo-electron microscopy; and wherein the protein is a candidate antibody therapeutic and its structure is pre-determined by a computational modeling process that comprises the steps of:
      i) providing amino acid sequences for framework regions (FR) and complementarity determining regions (CDR) in a set of antibody Fabs for which the 3D structure has been experimentally determined;
      ii) aligning, for a first FR in the candidate antibody and the corresponding FR in each provided Fab, the amino acid sequences to identify each Fab FR that shares at least 85% sequence identity with the candidate antibody FR and selecting the 3D structure of the Fab FR that has the highest sequence identity with the candidate antibody FR for use as the structural model for the first FR
      iii) repeating step (ii) for each FR in the candidate antibody;
      iv) aligning, for a first CDR in the candidate antibody and corresponding CDR in each provided Fab, the CDR amino acid sequences and selecting, for use as the structural model for the FR of interest, the 3D structure of the Fab CDR that has about the same length as the candidate antibody CDR and is likely to form a higher ordered structure;
      v) repeating step (iv) for each CDR in the candidate antibody;
      vi) grafting together the 3D structures of the selected Fab FRs and Fab CDRs and mutating the FR and CDR amino acid sequences in the grafted structure to be the same as in the candidate antibody to derive a Fab structural model of the candidate antibody;
      vii) superimposing two copies of the Fab structural model onto the structure of a full length IgG antibody with an Fc of the same isotype as the candidate antibody;
      viii) joining the two Fab copies with the Fc using a linker that is modeled to provide the appropriate disulfide bonds and thereby derive a full-length structural model of the candidate antibody; and
      ix) performing a molecular dynamics simulation on the full-length structural model that packs the side chains and eliminates any clashes in the structure to generate an energy minimized structure of the candidate antibody,
   b) selecting at least one region of the 3D protein structure to probe for potential sites of non-specific inter-molecular interactions between monomers of the protein and between monomers of the protein and at least one molecule of the test excipient;
   c) protonating the selected protein region to a desired pH;
   d) conducting a first probe-protein docking simulation over the entire surface area of the selected protein region, using as a first probe the 3D protein structure, to identify a set of one or more protein-protein docking sites whose docking scores in total equal −3 kcal/mol or lower;
   e) conducting a second probe-protein docking simulation over the entire surface area of the selected protein region, using as a second probe the 3D excipient structure, to identify any excipient-protein docking sites and classifying for further analysis as a putative protein-excipient complex each identified site that has a docking score that is −3 kcal/mol or lower, wherein each of the first and second probe-protein docking simulations may be conducted in either order or simultaneously;
   f) conducting a third probe-protein docking simulation over the entire surface area of each protein-excipient complex classified in step (e), using as a third probe at least one molecule of the 3D protein structure, and at all orientations of the protein, to identify each docking site for the protein on the protein-excipient complex that overlaps with any of the protein-protein docking sites identified in step (d) and classifying each overlapping site as a protein-excipient-protein sandwich; and
   g) selecting the test excipient as a candidate excipient to reduce aggregation of the protein in the formulation if at least one protein-excipient-protein sandwich classified in step (f) has a docking score that represents a lower binding affinity than the docking score for the protein-protein docking site in the sandwich.

2. The method of claim 1, wherein the resolution is at the atomic level or is at an intermediate level.

3. The method of claim 1, wherein the resolution is at the atomic level and the method further comprises conducting, before step (f), a molecular dynamics simulation on each putative protein-excipient complex classified in step (e) and retaining for use in step (f) each protein-excipient complex that has a binding free energy of −3 kcal/mol or lower.

4. The method of claim 1, wherein the 3D structure of the protein is obtained from a protein structure database.

5. The method of claim 4, wherein the protein structure is pre-determined experimentally and the database is the Protein Data Bank (PDB).

6. The method of claim 1, wherein the excipient is an amino acid.

7. The method of claim 1, wherein the formulation is a liquid formulation.

8. The method of claim 7, wherein the excipient is an amino acid.

9. The method of claim 1, wherein the first and second probe docking simulations are performed for at least two antibody regions selected from the group consisting of all light chain CDRs, all heavy chain CDRs, each Fab, the Fc region and the entire antibody.

10. The method of claim 1, wherein the 3D excipient structure is protonated to the same pH as the selected protein region.

11. The method of claim 1, further comprising examining in vitro the ability of the candidate excipient to reduce aggregation of the protein in the formulation.

12. A non-transitory machine-readable medium for carrying out the method of claim 1, comprising machine-readable instructions encoded thereon which, when executed by a processor, cause a machine having or linked to the processor to execute the method.

13. A computer system comprising the non-transitory machine-readable medium of claim 12 and a user interface capable of receiving the 3D structures of the protein and excipients and user selected criteria applied in one or more steps of the method.

* * * * *